United States Patent
Nishimura

(10) Patent No.: US 10,345,230 B2
(45) Date of Patent: Jul. 9, 2019

(54) SPECTROSCOPIC ANALYZER AND SPECTROSCOPIC ANALYSIS METHOD

(71) Applicant: HORIBA, Ltd., Kyoto (JP)

(72) Inventor: Katsumi Nishimura, Kyoto (JP)

(73) Assignee: HORIBA, LTD., Kyoto (JP)

( * ) Notice: Subject to any disclaimer, the term of this patent is extended or adjusted under 35 U.S.C. 154(b) by 158 days.

(21) Appl. No.: 15/490,507

(22) Filed: Apr. 18, 2017

(65) Prior Publication Data
US 2017/0299505 A1    Oct. 19, 2017

(30) Foreign Application Priority Data

Apr. 18, 2016 (JP) .................. 2016-083015

(51) Int. Cl.
| | |
|---|---|
| *G06F 11/30* | (2006.01) |
| *G01N 21/3504* | (2014.01) |
| *G01N 33/00* | (2006.01) |
| *G01J 3/02* | (2006.01) |
| *G01N 21/27* | (2006.01) |

(Continued)

(52) U.S. Cl.
CPC ........ *G01N 21/3504* (2013.01); *G01J 3/0297* (2013.01); *G01N 21/274* (2013.01); *G01N 33/004* (2013.01); *G01N 33/0037* (2013.01); *G01N 2021/3595* (2013.01); *G01N 2201/127* (2013.01); *G06T 11/206* (2013.01); *Y02A 50/245* (2018.01)

(58) Field of Classification Search
CPC .................................................. G01N 21/3504
See application file for complete search history.

(56) References Cited

U.S. PATENT DOCUMENTS

2011/0285998 A1* 11/2011 Hara .................. G01N 21/3504
356/437

FOREIGN PATENT DOCUMENTS

| | | | |
|---|---|---|---|
| JP | 09-101257 A | | 4/1997 |
| JP | 09-145607 | * | 6/1997 |

(Continued)

OTHER PUBLICATIONS

EESR dated Aug. 9, 2017 issued in European patent application No. 17 166 284.4.

*Primary Examiner* — Phuong Huynh
(74) *Attorney, Agent, or Firm* — Brooks Kushman P.C.

(57) ABSTRACT

The present invention is a spectroscopic analyzer that when measuring the concentration of a predetermined component contained in sample gas in a reduced pressure state lower than atmospheric pressure, obtains the concentration of the predetermined component with accuracy. The spectroscopic analyzer is one that measures the absorbance of the predetermined component contained in the sample gas in a reduced pressure state lower than atmospheric pressure, and calculates the concentration of the predetermined component with use of a calibration curve indicating the relationship between the absorbance of the predetermined component and the concentration of the predetermined component and a relational expression between the pressure of the sample gas at the time of the measurement and the concentration of the predetermined component. In addition, in a graph with one axis as pressure axis and the other axis as concentration axis, the relational expression has an intersection point other than zero with the pressure axis.

5 Claims, 4 Drawing Sheets

(51) Int. Cl.
 *G01N 21/35* (2014.01)
 *G06T 11/20* (2006.01)

(56) References Cited

FOREIGN PATENT DOCUMENTS

| | | |
|---|---|---|
| JP | 09145607 A | 6/1997 |
| JP | 2003014632 A | 1/2003 |
| JP | 2010066209 A | 3/2010 |

* cited by examiner

SPECTROSCOPIC ANALYZER AND SPECTROSCOPIC ANALYSIS METHOD

CROSS-REFERENCE TO RELATED APPLICATION

This application claims priority to JP Application No. 2016-083015, filed Apr. 18, 2016, the disclosure of which is incorporated in its entirety by reference herein.

TECHNICAL FIELD

The present invention relates to a spectroscopic analyzer using infrared spectroscopy such as Fourier transform infrared spectroscopy.

BACKGROUND ART

In the past, as an analyzer adapted to measure the concentration of a predetermined component contained in sample gas such as exhaust gas, there has been one using, for example, Fourier transform infrared (FTIR) spectroscopy (Patent Literature 1).

In the analyzer using the FTIR spectroscopy, a pump is provided on the upstream side of a measurement cell, and the pressure of sample gas in the measurement cell is atmospheric pressure or a pressure close to atmospheric pressure. That is, the pressure at the time of sample gas measurement is atmospheric pressure or a pressure close thereto.

In addition, the concentration of a predetermined component is obtained by performing concentration calculation using a calibration curve obtained from the relationship between multiple known gas concentrations and corresponding absorbances and making a correction based on the pressure of the sample gas because the pressure of the sample gas at the time of measurement affects the concentration.

As described above, since the pressure of the sample gas at the time of measurement is atmospheric pressure or a pressure close to atmospheric pressure, as the calibration curve, one prepared at atmospheric pressure is used. In this case, the concentration correction based on the pressure is made using a linear relational expression passing through the origin on the assumption that the relationship between pressure and concentration is a simple proportional relationship. This is because, usually, on the assumption that since the pressure at the time of measurement is close to atmospheric pressure, the effect of pressure broadening is small, and absorbance changes in proportion to the partial pressure of the gas, the correction is made using the linear relational expression having no intercept. Specifically, the pressure correction is made using the following expression.

$$C_{x\_press} = C_x \times \frac{a_x}{P} \quad \text{[Expression 1]}$$

where $C_{x\_press}$ is the concentration of a component x after the pressure correction, $a_x$ is a pressure correction coefficient for the component x (usually $a_x = P_0$: reference pressure), P: is the pressure inside a measurement cell [kPa], and $C_x$ is the concentration of the component x before the pressure correction.

CITATION LIST

Patent Literature

Patent Literature 1: JP-A-09-101257

SUMMARY OF INVENTION

Technical Problem

Meanwhile, in the configuration adapted to arrange the pump on the upstream side of the measurement cell to compressively feed the exhaust gas, in order to prevent the condensation of moisture contained in the exhaust gas, the pump is heated to high temperature, and depending on heating temperature, the flow rate of the exhaust gas varies, thus causing the problem of difficulty in controlling the flow rate.

For this reason, the present inventor is considering a configuration adapted to arrange a pump on the downstream side of a measurement cell to suck exhaust gas, and thereby eliminate heating the pump or reduce heating temperature.

However, the present inventor has acquired knowledge that in the configuration adapted to arrange the pump on the downstream side of the measurement cell, the sample gas inside the measurement cell is brought to a reduced pressure state, and the conventional linear relational expression having no intercept does not allow accurate pressure correction. This has been obtained by clarifying that as a result of plotting concentrations not subjected to pressure correction while slightly changing pressure under reduced pressure (see FIG. 4), when measuring concentration with the pressure increased by approximately 2 kPa, the resulting concentration value is higher than that obtained using the conventional linear relational expression, whereas when measuring concentration with the pressure decreased by approximately 2 kPa, the resulting concentration value is lower than that obtained using the conventional linear relational expression, and 1% or less of a full scale (FS) as a standard is not satisfied. This problem clearly appeared in particular when a high concentration CO component and $CO_2$ component were measured.

Therefore, the present invention is made in order to solve the above problems at once, and a main object thereof is to, when measuring the concentration of a predetermined component contained in sample gas in a reduced pressure state lower than atmospheric pressure, obtain the concentration of the predetermined component with accuracy.

Solution to Problem

That is, a spectroscopic analyzer according to the present invention is one that measures the concentration of a predetermined component contained in sample gas, and the spectroscopic analyzer measures the absorbance of the predetermined component contained in the sample gas in a reduced pressure state lower than atmospheric pressure, and calculates the concentration of the predetermined component with use of a calibration curve indicating the relationship between the absorbance of the predetermined component and the concentration of the predetermined component and a relational expression between the pressure of the sample gas at the time of the measurement and the concentration of the predetermined component. In addition, in a graph with one axis as pressure axis and the other axis as concentration axis, the relational expression has an intersection point other than zero with the pressure axis.

Also, a spectroscopic analysis method according to the present invention is one adapted to measure the concentration of a predetermined component contained in sample gas, and the spectroscopic analysis method measures the absorbance of the predetermined component contained in the sample gas in a reduced pressure state lower than atmospheric pressure, and calculates the concentration of the predetermined component with use of a calibration curve indicating the relationship between the absorbance of the predetermined component and the concentration of the predetermined component and a relational expression between the pressure of the sample gas at the time of the measurement and the concentration of the predetermined component. In addition, in a graph with one axis as pressure axis and the other axis as concentration axis, the relational expression has an intersection point other than zero with the pressure axis.

It is desirable that the relational expression represents a linear relationship in a graph with an X axis as pressure axis and a Y axis as concentration axis. And it is desirable that the relational expression represents a quadratic relationship in a graph with an X axis as pressure axis and a Y axis as concentration axis.

Advantageous Effects of Invention

According to the present invention configured as described, a pressure correction of the concentration of the predetermined component measured under the reduced pressure condition lower than atmospheric pressure is made using the relational expression representing the linear relationship or the quadratic relationship between the pressure of the sample gas at the time of the measurement and the concentration of the predetermined component and having an intersection point other than zero with the pressure axis, and therefore when measuring the concentration of the predetermined component contained in the sample gas in the reduced pressure state lower than atmospheric pressure, the concentration of the predetermined component can be obtained with accuracy.

DESCRIPTION OF EMBODIMENTS

In the following, one embodiment of an infrared spectroscopic analyzer according to the present invention will be described with reference to drawings.

An infrared spectroscopic analyzer 100 in the present embodiment is an exhaust gas analyzer adapted to measure, as pieces of time series data, the concentrations of multiple components contained in exhaust gas as sample gas discharged from an internal combustion engine such as the engine of an automobile.

Figure 1:
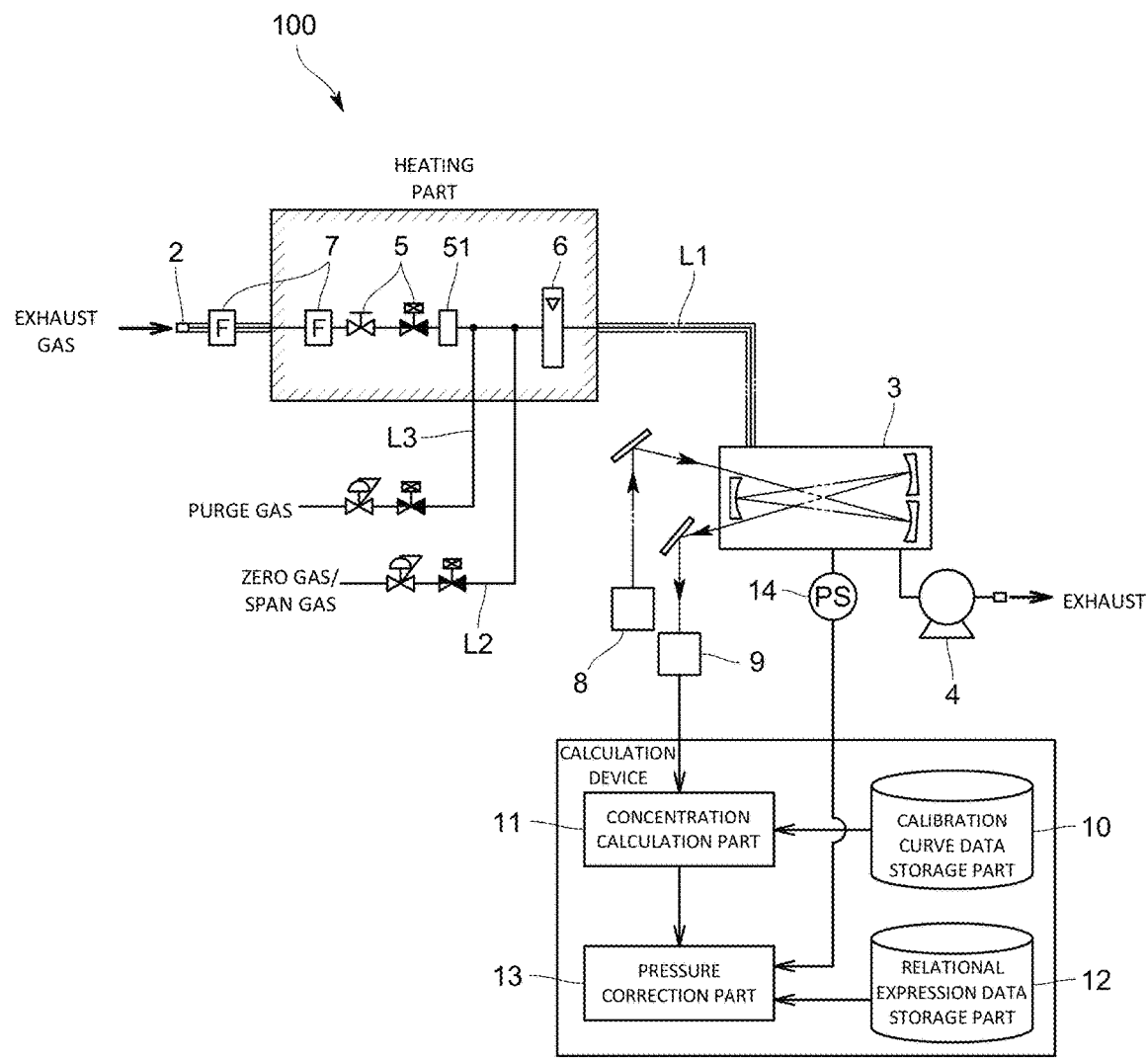
FIG. 1 is a schematic diagram illustrating the configuration of an infrared spectroscopic analyzer in the present embodiment.

Specifically, the infrared spectroscopic analyzer 100 is one that as illustrated in FIG. 1, collects a part or the whole of exhaust gas discharged from, for example, the tail pipe of an automobile through a sample collection part 2, introduced the exhaust gas collected through the sample collecting part 2 into a measurement cell 3 without dilution, and measures the concentrations of multiple components such as carbon monoxide (CO), carbon dioxide ($CO_2$), nitrogen monoxide (NO), nitrogen dioxide ($NO_2$), nitrogen oxides ($NO_x$), and water ($H_2O$) in the exhaust gas by FTIR spectroscopy.

In addition, in the infrared spectroscopic analyzer 100, in an exhaust gas line L1 provided with the measurement cell 3, a suction pump 4 for introducing the exhaust gas into the measurement cell 3 is provided on the downstream side of the measurement cell 3. Also, in the exhaust gas line L1, valves 5 and orifice 51 for regulating the flow rate of the exhaust gas, a flowmeter 6 for measuring the flow rate of the exhaust gas, a filter 7 for removing dust in the exhaust gas, and the like are provided. Further, the exhaust gas line L1 or the measurement cell 3 is connected with: a reference gas supply line L2 for supplying zero gas and span gas for calibrating a light detector 9 to the measurement cell 3: and a purge gas line L3 for purging the exhaust gas line L1 or the measurement cell 3.

Still further, the infrared spectroscopic analyzer 100 includes: an interferometer 8 that radiates interfered infrared light towards the measurement cell 3; and the light detector 9 that detects the intensity of light emitted through the measurement cell 3. The infrared spectroscopic analyzer 100 calculates the infrared absorption spectrum of the exhaust gas using light intensity signals obtained by the light detector 9, and from absorbances in the infrared absorption spectrum, calculates the concentrations of the multiple components.

Note that the sample gas introduced into the measurement cell 3 is sucked by the suction pump 4, and therefore in a state depressurized to a pressure (75 kPa to 85 kPa) lower than atmospheric pressure. For this reason, the infrared spectroscopic analyzer 100 includes: a calibration curve data storage part 10 that stores calibration curve data indicating the relationship between the absorbance of a predetermined component and the concentration of the predetermined component; a concentration calculation part 11 that calculates the concentration of the predetermined component from absorbance in the infrared absorption spectrum and a calibration curve indicated by the calibration curve data; a relational expression data storage part 12 that stores relational expression data indicating the relationship between the pressure of the sample gas at the time of measurement and the concentration of the predetermined component; and a pressure correction part 13 that corrects the concentration of the component from the pressure of the sample gas at the time of the measurement and a relational expression indicated by the relational expression data.

Note that the calibration curve data storage part 10 stores pieces of calibration curve data prepared at a predetermined pressure (e.g., a reference pressure). A calibration curve indicated by each of the pieces of calibration curve data is one that determines the relationship between the concentrations (multiple representative values, and for example, in the case of CO, concentrations of 2%, 4%, 6%, 8%, and so on) of each component and corresponding absorbances.

Also, the relational expression data storage part 12 stores pieces of relational expression data each of which indicates the relationship between the pressure of the sample gas at the time of measurement and the concentration of a predetermined component. A relational expression indicated by each of the pieces of relational expression data is one representing a straight line and having an intersection point (Hereinafter, in this embodiment, referred to as pressure coefficient) other than zero with the pressure axis. That is, the relational expression represents the straight line not passing through the origin. In addition, the relational expression data storage part 12 may be one that stores data indicating the pressure coefficient of the relational expression.

Figure 2:
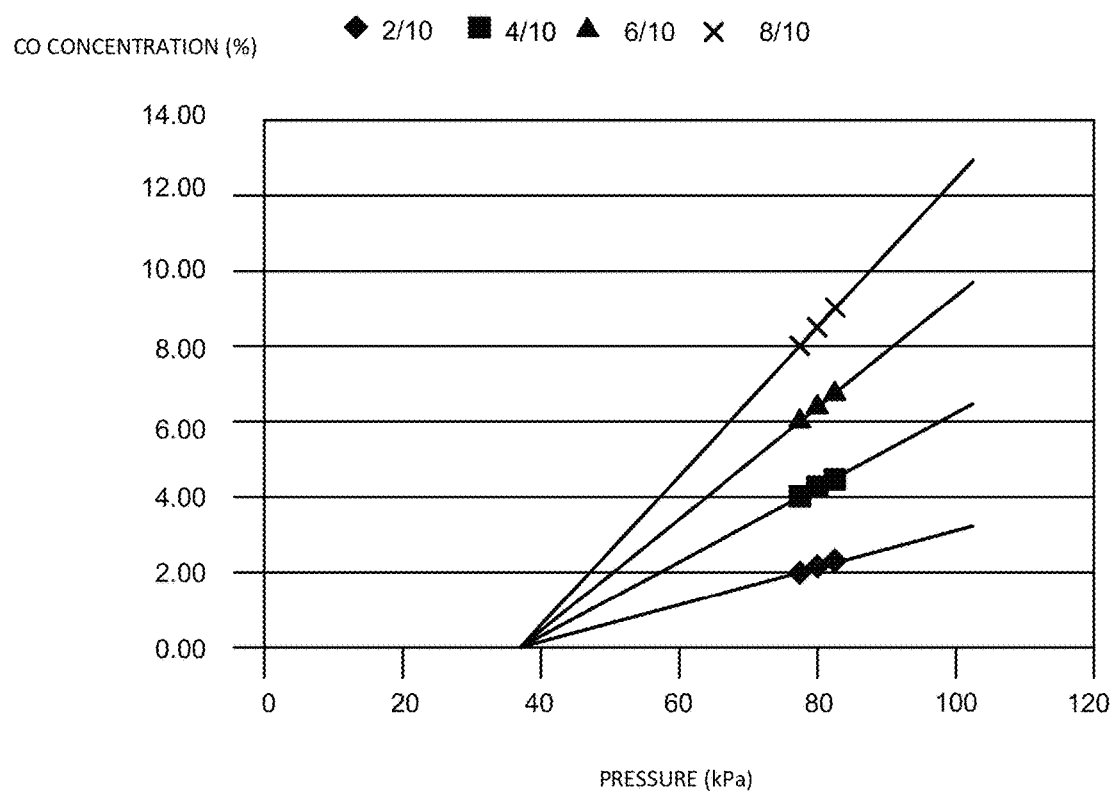
FIG. 2 is a graph illustrating relational expressions between pressure and concentration before correction in the same embodiment.

FIG. 2 illustrates the relationships between pressure and concentrations not subjected to pressure correction obtained when measuring four levels of CO concentrations at reduced pressures of 78 kPa, 80 kPa, and 82 kPa using standard gas having a known CO concentration. Note that the graph of FIG. 2 is illustrated with the X axis as pressure and the Y axis as CO concentration.

As can be seen from the graph of FIG. 2, relational expressions for the respective CO concentration levels all represent straight lines and have X intercepts (not passing through the origin). In addition, it turns out that the relational expressions for the respective CO concentration levels all intersect with one another at a CO concentration of zero, and the X intercepts of the relational expressions for the respective concentration levels take almost the same value.

The pressure correction part 13 acquires concentration before the pressure correction from the concentration calculation part 11 and also acquires pressure at the time of measurement from a pressure sensor 14 adapted to measure the pressure of the sample gas in the measurement cell 3. Further, the pressure correction part 13 acquires corresponding relational expression data from the relational expression data storage part 12. Note that the pressure sensor 14 is provided in a part where the pressure of the sample gas in the measurement cell 3 can be measured, and provided in the measurement cell 3.

In addition, the pressure correction part 13 makes the pressure correction of the concentration acquired from the concentration calculation part 11 in accordance with the following expression.

$$C_{x\_press} = C_x \times \frac{(a_x - Px\_c)}{(P - Px\_c)} \quad \text{[Expression 2]}$$

where $C_{x\_press}$ is the concentration of a component x after the pressure correction, $a_x$ is a pressure correction constant number for the component x (normally, $a_x = P_0$: reference pressure), P is the pressure inside the measurement cell [kPa], $C_x$ is the concentration of the component x before the pressure correction, and Px_c is a pressure coefficient for the component x [kPa] (the X intercept of a relational expression).

Note that Px_c is set for each of the calibration lines for the respective components, and the value of Px_c is stored in the relational expression data storage part 12. The default value of Px_c is zero. Equivalent concentration in each spectrum at the time of calibration curve preparation is calculated in the conventional manner, i.e., using Px_c=0. Px_c is obtained from indicated values obtained without pressure correction when variously changing pressure while flowing the span gas after the calibration curve preparation.

Next, the concentrations after the pressure correction (Table 2 below) obtained by the infrared spectroscopic analyzer 100 configured as described above are listed relative to the concentrations before the pressure correction (Table 1 below). Note that the pieces of data below are results of CO concentration measurement performed on respective gases 1/10 (1% concentration), 2/10 (2% concentration), . . . , 10/10 (10% concentration) obtained by dividing the standard gas (span gas) having the known CO concentration (10%) into 10 portions. In addition, the calibration curves are prepared at the standard pressure of 100 kPa after measuring calibration curve spectra at 80 kPa.

When comparing Table 1 (concentrations before correction) and Table 2 (concentration after correction), it turns out from Table 2 that for 80 kPa, 82 kPa, and 84 kPa, concentration calculation results are almost coincident for each of the gases, and the pressure correction is made with accuracy. Note that regarding the pieces of 10/10 data in Table 2 (concentrations after correction), at the times of measurement at 82 kPa and 84 kPa, some kind of abnormality occurred, and therefore the corrected values are considered not to be coincident. Also, corrected values in Table 2 (concentrations after correction) are not coincident with the cylinder concentration at the reference pressure of 100 kPa (CO concentration of standard gas). This is because the measured values after the pressure correction are not subjected to span sensitivity calibration, and the measured values can be matched with the cylinder concentration by performing the span sensitivity calibration.

TABLE 1

| Pressure | 1/10 | 2/10 | 3/10 | 4/10 | 5/10 | 6/10 | 7/10 | 8/10 | 9/10 | 10/10 |
|---|---|---|---|---|---|---|---|---|---|---|
| 80 | 0.98 | 1.93 | 2.90 | 3.87 | 4.85 | 5.83 | 6.80 | 7.78 | 8.78 | 9.79 |
| 82 | 1.03 | 2.02 | 3.04 | 4.06 | 5.08 | 6.10 | 7.13 | 8.16 | 9.20 | 12.09 |
| 84 | 1.07 | 2.11 | 3.17 | 4.24 | 5.31 | 6.39 | 7.45 | 8.54 | 9.64 | 12.54 |
| 100 | 1.16 | 2.32 | 3.48 | 4.54 | 5.80 | 6.95 | 8.11 | 9.27 | 10.43 | 11.59 |

TABLE 2

| Pressure | 1/10 | 2/10 | 3/10 | 4/10 | 5/10 | 6/10 | 7/10 | 8/10 | 9/10 | 10/10 |
|---|---|---|---|---|---|---|---|---|---|---|
| 80 | 1.45 | 2.85 | 4.28 | 5.71 | 7.15 | 8.61 | 10.04 | 11.49 | 12.96 | 14.45 |
| 82 | 1.45 | 2.85 | 4.28 | 5.72 | 7.16 | 8.60 | 10.04 | 11.50 | 12.97 | 17.04 |
| 84 | 1.45 | 2.85 | 4.28 | 5.72 | 7.16 | 8.61 | 10.04 | 11.51 | 12.99 | 16.90 |
| 100 | 1.16 | 2.32 | 3.48 | 4.64 | 5.80 | 6.95 | 8.11 | 9.27 | 10.43 | 11.59 |

In the infrared spectroscopic analyzer 100 in the present embodiment configured as described above, since the pressure correction of the concentration of a predetermined component measured under a reduced pressure condition lower than atmospheric pressure is made using a relational expression representing the linear relationship between the pressure of the sample gas at the time of measurement and the concentration of the predetermined component and an intersection point other than zero with the pressure axis, when measuring the concentration of the predetermined component contained in the sample gas in a reduced pressure state lower than atmospheric pressure, the concentration of the predetermined component can be obtained with accuracy.

Note that the present invention is not limited to the above-described embodiment.

In the above-described embodiment, the relational expression for CO is exemplified; however, it should be appreciated that for each of the other components contained in the exhaust gas, such as $CO_2$, $NO$, $NO_2$, and $H_2O$, a relational expression can also be prepared in the same manner to make a pressure correction.

In addition, the relational expression in the above-described embodiment does not have to establish a strict linear relationship. Also, it is not necessary to establish a relationship an intersection point other than zero with the pressure axis over the entire pressure range, and it is only necessary to establish a linear relationship an intersection point other than zero with the pressure axis within a predetermined range (e.g., 75 to 85 kPa) where pressure at the time of measurement varies. Further, in order to reduce a pressure variation range at the time of measurement, a pressure variation preventing mechanism such as a regulator may be provided on the upstream side of the measurement cell 3.

The effect of pressure variation can be corrected by the above-described embodiment; however, when examining the linearity of a calibration curve in a state where a new pressure correction coefficient is set, an error may increase in proportion to concentration to cause deviation from a standard. For this reason, in addition to the pressure correction in the above-described embodiment, the pressure correction part 13 makes a pressure correction of the concentration obtained by the concentration calculation part 11 in accordance with the following expression.

$$C_{x\_press} = C_x \times \frac{(a_x - \text{Px\_c})}{(P - \text{Px\_c})} \times \text{Px\_a} \qquad [\text{Expression 3}]$$

where $C_{x\_press}$ is the concentration of the component x after the pressure correction, $a_x$ is the pressure correction constant number for the component x (normally, $a_x = P_0$: reference pressure), P is the pressure inside the measurement cell [kPa], $C_x$ is the concentration of the component x before the pressure correction, Px_c is the pressure coefficient for the component x [kPa] (the X intercept of the relational expression), and Px_a is a linearity correction coefficient.

Note that Px_c is set for each of the calibration curves for the respective components, and the value of Px_c is stored in the relational expression data storage part 12. The default value of Px_c is 0. Equivalent concentration in each spectrum at the time of the calibration curve preparation is calculated in the conventional manner, i.e., using Px_c=0. Px_c is obtained from indicated values obtained without pressure correction when changing pressure several times while flowing the span gas after the calibration curve preparation.

Also, Px_a is set for each of the calibration curves for the respective components, and the value of Px_a is stored in the relational expression data storage part 12. The default value of Px_a is 1. When Px_c is 0 at the time of the calibration curve preparation, the value is set to 1, and when Px_c is not 0, the value is calculated by the following method. Note that the value is normally automatically calculated, but may be set to an arbitrary value.

<Calculation Method for Px_a>

To prepare a calibration curve, after preparing a calibration curve matrix, a Px_a calculation process is added. The representative spectrum of the measurement component is used to calculate Px_a in accordance with the following expression. In addition, when Px_c is 0 or the pressure correction is invalid, Px_a is set as Px_a=1, and the calculation is not performed.

$$\text{Px\_a} = \frac{C_{x\_orig}}{C_x} \qquad [\text{Expression 4}]$$

where $C_{x\_orig}$ is the concentration (cylinder value) of the measurement component x in the representative spectrum, $C_x$ is the concentration of the measurement component x calculated with the representative spectrum as input.

For the pressure correction, the calculation is performed with Px_a=1.

In addition, the representative spectrum refers to a final measured spectrum used to calculate the calibration curve matrix, and when two or more types of concentration data are present, refers to the second highest concentration data.

Next, the following table lists linearity results obtained in the infrared spectroscopic analyzer 100 configured as described above when Px_c is set and when the correction is made with Px_a at the time of the calibration curve preparation at the reference pressure of 80 kPa for the standard gas (span gas) having the known CO concentration (10%).

TABLE 3

| | | Reference pressure 80 kPa<br>Px_c = 0.0<br>Px_a = 1.0 | | Reference pressure 80 kPa<br>Px_c = 37.9<br>Px_a = 1.0 | | Reference pressure 80 kPa<br>Px_c = 37.9<br>Px_a = 1.0146 | |
|---|---|---|---|---|---|---|---|
| Reference concentration [%] | Measurement concentration [%] | Error [%] (FS) | Measurement concentration [%] | Error [%] (FS) | Measurement concentration [%] | Error [%] (FS) |
| 1/10 | 1.16 | 1.17 | 0.08 | 1.15 | 0.10 | 1.17 | 0.07 |
| 2/10 | 2.32 | 2.31 | 0.10 | 2.28 | 0.44 | 2.31 | −0.07 |
| 3/10 | 3.48 | 3.47 | 0.09 | 3.42 | 0.61 | 3.47 | −1.10 |
| 4/10 | 4.64 | 4.64 | 0.03 | 4.57 | 0.73 | 4.64 | −0.03 |
| 5/10 | 5.80 | 5.81 | 0.03 | 5.72 | 0.84 | 5.80 | 0.04 |
| 6/10 | 6.97 | 6.97 | 0.09 | 6.87 | 0.95 | 6.97 | 0.00 |

TABLE 3-continued

| | Reference pressure 80 kPa Px_c = 0.0 Px_a = 1.0 | | Reference pressure 80 kPa Px_c = 37.9 Px_a = 1.0 | | Reference pressure 80 kPa Px_c = 37.9 Px_a = 1.0146 | |
|---|---|---|---|---|---|---|
| Reference concentration [%] | Measurement concentration [%] | Error [%] (FS) | Measurement concentration [%] | Error [%] (FS) | Measurement concentration [%] | Error [%] (FS) |
| 7/10  8.13 | 8.13 | 0.06 | 8.01 | 1.16 | 8.13 | −0.03 |
| 8/10  9.29 | 9.29 | 0.05 | 9.15 | 1.34 | 9.28 | −0.06 |
| 9/10  10.45 | 10.45 | 0.03 | 10.30 | 1.53 | 10.45 | 0.00 |
| 10/10 11.61 | 11.63 | 0.22 | 11.46 | 1.51 | 11.63 | 0.17 |

In the case of Px_a=1.0 and Px_c=37.9, it turns out that higher concentrations deviate from the standard (±1% FS); however, by correcting the linearity of a calibration curve using Px_a=1.0146, even higher concentrations fall within the standard (±1% FS).

Figure 3:
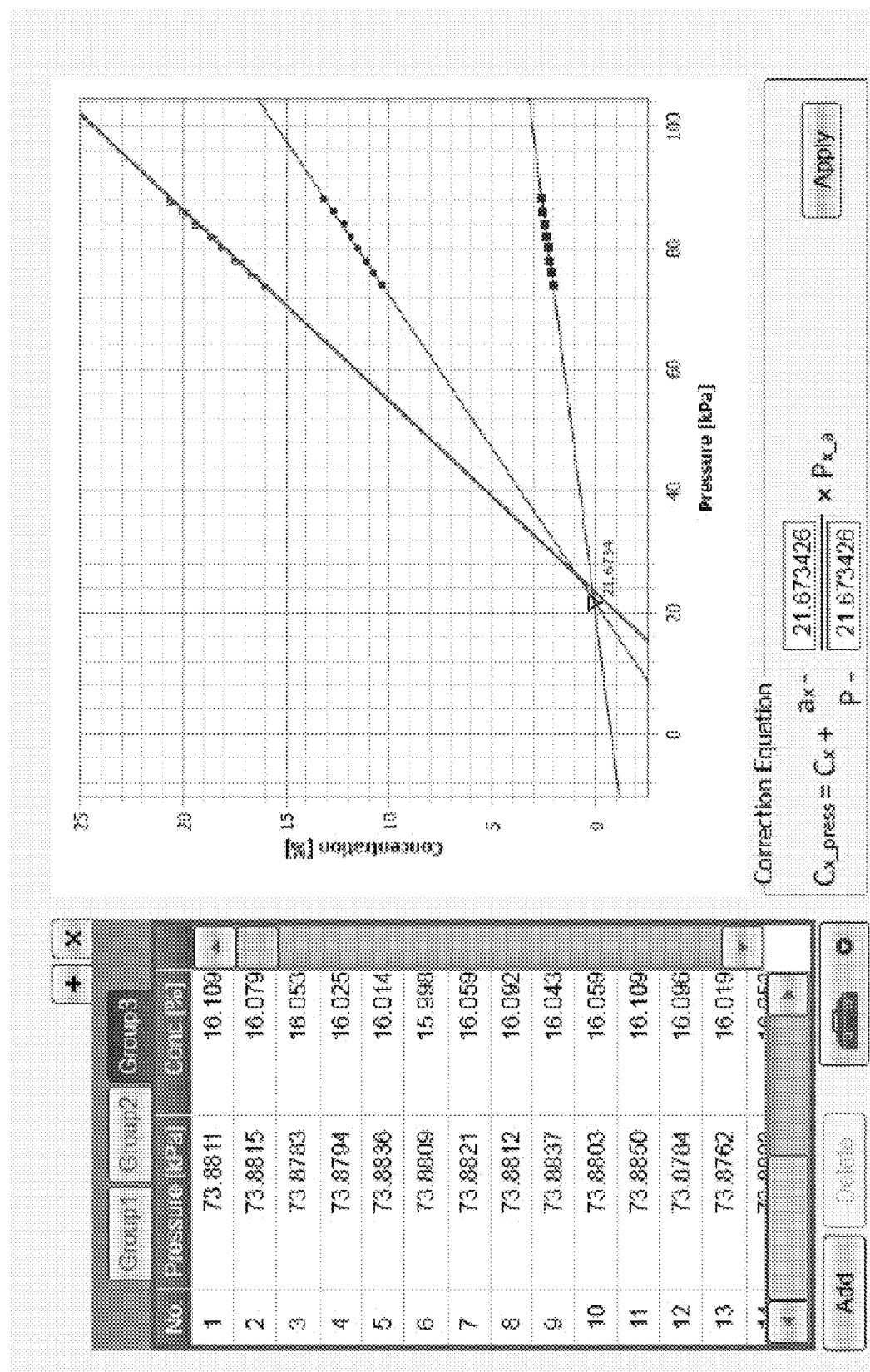
FIG. 3 is a diagram illustrating a screen display of relational expressions by calculation software in a variation.
Figure 4:
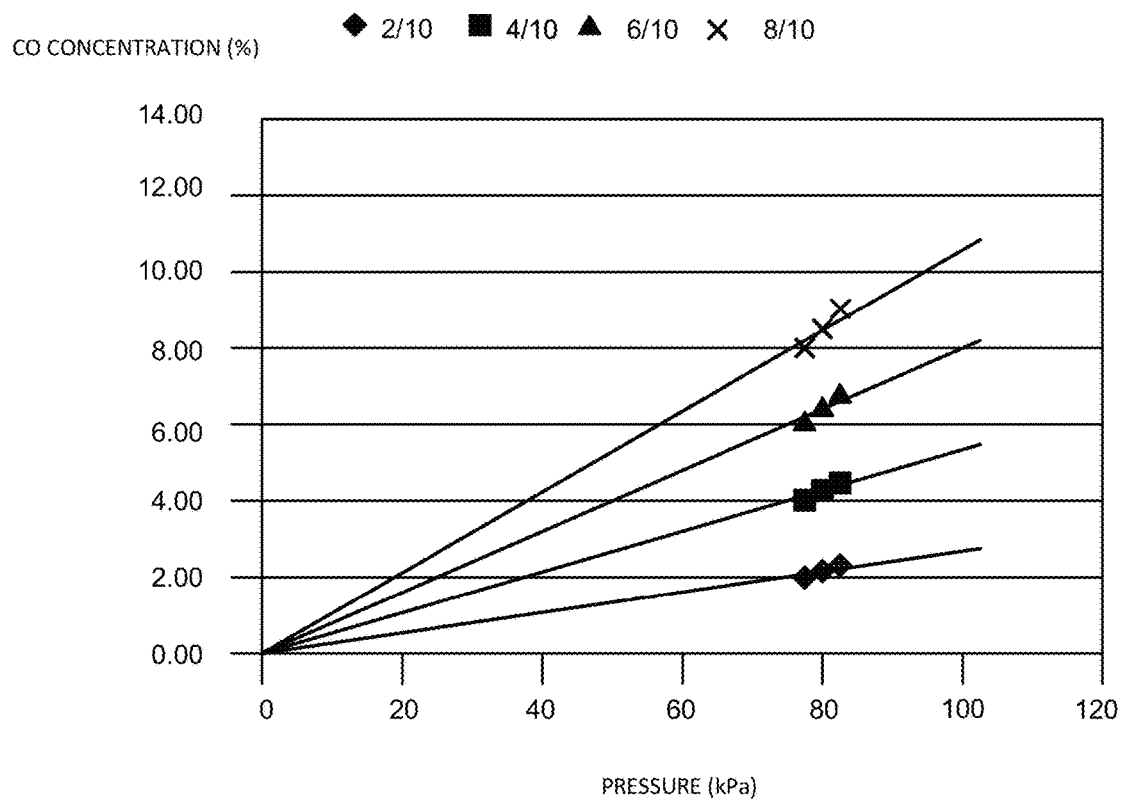
FIG. 4 is a graph illustrating relational expressions between pressure and concentration before correction in a conventional infrared spectroscopic analyzer.

In addition, the infrared spectroscopic analyzer 100 may be one having a pressure coefficient calculation part that automatically calculates the pressure coefficient [kPa] for the measurement component x from multiple pieces of relational expression data. Note that in this case, the infrared spectroscopic analyzer 100 displays a screen illustrated in FIG. 3 on a display.

The pressure coefficient calculation part obtains the pressure coefficient from measured concentrations without pressure correction by measuring the concentration of each of calibration gases having different concentrations while variously changing pressure. That is, the pressure coefficient calculation part acquires and reads groups of pieces of data belonging to multiple measurement result groups including a group of pieces of measurement result data obtained by measuring the concentration of a calibration gas having a first concentration while changing pressure ("Group 1"), a group of pieces of measurement result data obtained by measuring the concentration of a calibration gas having a second concentration while changing pressure ("Group 2"), and a group of pieces of measurement result data obtained by measuring the concentration of a calibration gas having a third concentration while changing pressure ("Group 3") (see the left-side table in FIG. 3). Note that a user may set the groups of pieces of data belonging to the measurement result groups using input means.

Then, the pressure coefficient calculation part prepares relational expressions for the measurement result groups from the groups of pieces of data belonging to the groups (see the right-side graph in FIG. 3), respectively and correspondingly. As a result, the pressure coefficient calculation part calculates a pressure coefficient for each of the multiple relational expressions. In addition, when the pressure coefficient calculation part reads the groups of pieces of data belonging to the measurement result groups, a relational expression is automatically calculated and is displayed in the right-side graph.

Further, the pressure coefficient calculation part performs a predetermined calculation on the multiple pressure coefficients to calculate a representative pressure coefficient (such as an average value of them). The representative pressure coefficient is displayed in a calculation result column displayed on the lower side of the graph in FIG. 3. In response to predetermined input by a user, such as pressing the "Apply" button displayed in the calculation result column, the representative pressure coefficient is used as Px_a in Expression 2 or 3 described above.

In the above-described embodiment, the relational expression represents a linear relationship in a graph, but the relational expression may represent a quadratic relationship in a graph. In this case, the quadratic relational expression has an intersection point other than zero with the pressure axis. And the pressure coefficient is a pressure at an inflection point of the relational expression.

$$C_{x\_press} = C_x \times \left(\frac{(a_x - \text{Px\_c})}{(P - \text{Px\_c})}\right)^2 \times \text{Px\_a} \quad \text{[Expression 5]}$$

where $C_{x\_press}$ is the concentration of the component x after the pressure correction, $a_x$ is the pressure correction constant number for the component x (normally, $a_x=P_0$: reference pressure), P is the pressure inside the measurement cell [kPa], $C_x$ is the concentration of the component x before the pressure correction, Px_c is the pressure coefficient for the component x [kPa] (the pressure at the inflection point of the relational expression), and Px_a is a linearity correction coefficient.

In the above-described embodiment, a concentration calculation using a calibration curve and a pressure correction using a relational expression for the pressure correction are separately made, but may be made using one relational expression.

In addition, the relational expression represents a cubic relationship in a graph with an X axis as pressure axis and a Y axis as concentration axis.

In the above-described embodiment, the analyzer using the FTIR spectroscopy is described; however, an analyzer using NDIR spectroscopy may be applied.

In addition, the spectroscopic analyzer of the present invention is not limited to the one using infrared light, but may be one using ultraviolet light or visible light.

Further, in the above-described embodiment, described is the case where the present invention is applied to the exhaust gas analyzer adapted to analyze the exhaust gas discharged from the internal combustion engine; however, the present invention may be applied to an analyzer adapted to analyze exhaust gas discharged from a plant or a power generation facility or an analyzer adapted to analyze other sample gas.

Besides, needless to say, the present invention is not limited to any of the above-described embodiment and variations, but can be variously modified without departing from the scope thereof.

REFERENCE SIGNS LIST

100: Infrared spectroscopic analyzer
3: Measurement cell
4: Pump
8: Interferometer part
9: Light detecting part
10: Calibration curve data storage part 11: Concentration calculation part
12: Relational expression data storage part
13: Pressure correction part
14: Pressure sensor

What is claimed is:

1. An apparatus that measures concentration of a predetermined component contained in sample gas, comprising:
   a spectroscopic analyzer including
      a calibration curve data storage part that stores calibration curve data indicating a relationship between absorbance of a predetermined component and the concentration of the predetermined component,
      a concentration calculation part that calculates the concentration of the predetermined component based on the calibration curve data,
      a relational expression data storage part that stores relational expression data indicating a relationship between a pressure of the sample gas at time of measurement and the concentration of the predetermined component, and
      a pressure correction part that corrects the concentration of the predetermined component from the pressure of the sample gas at the time of the measurement and a relational expression indicated by the relational expression data, wherein
      in a graph with one axis as pressure axis and an other axis as concentration axis, the relational expression has an intersection point other than zero with the pressure axis.

2. The apparatus according to claim 1, wherein
   the relational expression represents a linear relationship in a graph with an X axis as pressure axis and a Y axis as concentration axis.

3. The apparatus according to claim 1, wherein
   the relational expression represents a quadratic relationship in a graph with an X axis as pressure axis and a Y axis as concentration axis.

4. The apparatus according to claim 1, wherein
   the sample gas is exhaust gas discharged from an internal combustion engine.

5. A spectroscopic analysis method adapted to measure concentration of a predetermined component contained in sample gas, comprising:
   by a spectroscopic analyzer,
      introducing the sample gas into a measurement cell with a suction pump,
      measuring a pressure of the sample gas in the measurement cell with a pressure sensor,
      measuring absorbance of the predetermined component contained in the sample gas in a reduced pressure slate lower than atmospheric pressure, and
      calculating the concentration of the predetermined component with use of a calibration curve indicating a relationship between absorbance of the predetermined component and concentration of the predetermined component and a relational expression between pressure of the sample gas at a time of measurement and the concentration of the predetermined component, wherein
      in a graph with one axis as pressure axis and an other axis as concentration axis, the relational expression has an intersection point other than zero with the pressure axis.

* * * * *